United States Patent [19]
Adobbati

[11] Patent Number: 5,445,618
[45] Date of Patent: Aug. 29, 1995

[54] SAFETY SYRINGE WITH NON-LINEAR NEEDLE

[76] Inventor: Ricardo N. Adobbati, 615 Palo Verde, Brownsville, Tex. 78520

[21] Appl. No.: 183,038

[22] Filed: Jan. 18, 1994

[51] Int. Cl.⁶ .................... A61M 5/32; A61M 5/31; A61M 5/00
[52] U.S. Cl. .................... 604/192; 604/240; 604/110
[58] Field of Search ............. 604/110, 187, 192, 195, 604/240; 128/763-765

[56] References Cited

U.S. PATENT DOCUMENTS

| | | | |
|---|---|---|---|
| 2,894,509 | 7/1959 | Bednarz | 604/192 |
| 4,941,883 | 7/1990 | Venturini | 604/195 |
| 5,000,167 | 3/1991 | Sunderland | 128/763 |
| 5,147,323 | 9/1992 | Haber et al. | 604/191 |
| 5,163,916 | 11/1992 | Sunderland | 604/198 |
| 5,188,119 | 2/1993 | Sunderland | 128/763 |
| 5,201,718 | 4/1993 | Whisson | 604/195 |
| 5,215,534 | 6/1993 | De Harde et al. | 604/110 |
| 5,232,456 | 8/1993 | Gonzalez | 604/192 |
| 5,246,427 | 9/1993 | Sturman et al. | 604/192 |
| 5,263,942 | 11/1993 | Smedley et al. | 604/110 |
| 5,267,973 | 12/1993 | Haber et al. | 604/110 |

FOREIGN PATENT DOCUMENTS 479303  4/1992  European Pat. Off. ............ 604/240

*Primary Examiner*—C. Fred Rosenbaum
*Assistant Examiner*—Frank Wilkens, III
*Attorney, Agent, or Firm*—Gunn, Lee & Miller

[57] ABSTRACT

A rectangular hypodermic syringe with a needle that can not be re-used once a nonlinear needle has been moved to a needle protecting retracted position includes a rectangular cylinder; a rectangular plunger for displacing the fluid within the cylinder; a rectangular needle guard, having an interior chamber, demountably attached to the rectangular cylinder; an elongate needle assembly, having a nonlinear needle, slidably mounted within the interior chamber of said needle guard; and means for fluidly coupling said cylinder to said needle when the needle assembly is in the extended position and for fluidly separating the cylinder from the needle when the needle assembly is in the retracted position. Lock means locks the needle assembly in the needle exposing extended position. Release means unlocks the needle assembly allowing a coil spring to move the needle assembly to the needle protecting retracted position. The spring keeps the needle in the needle protecting retracted position and from returning to the needle exposing extended position.

3 Claims, 4 Drawing Sheets

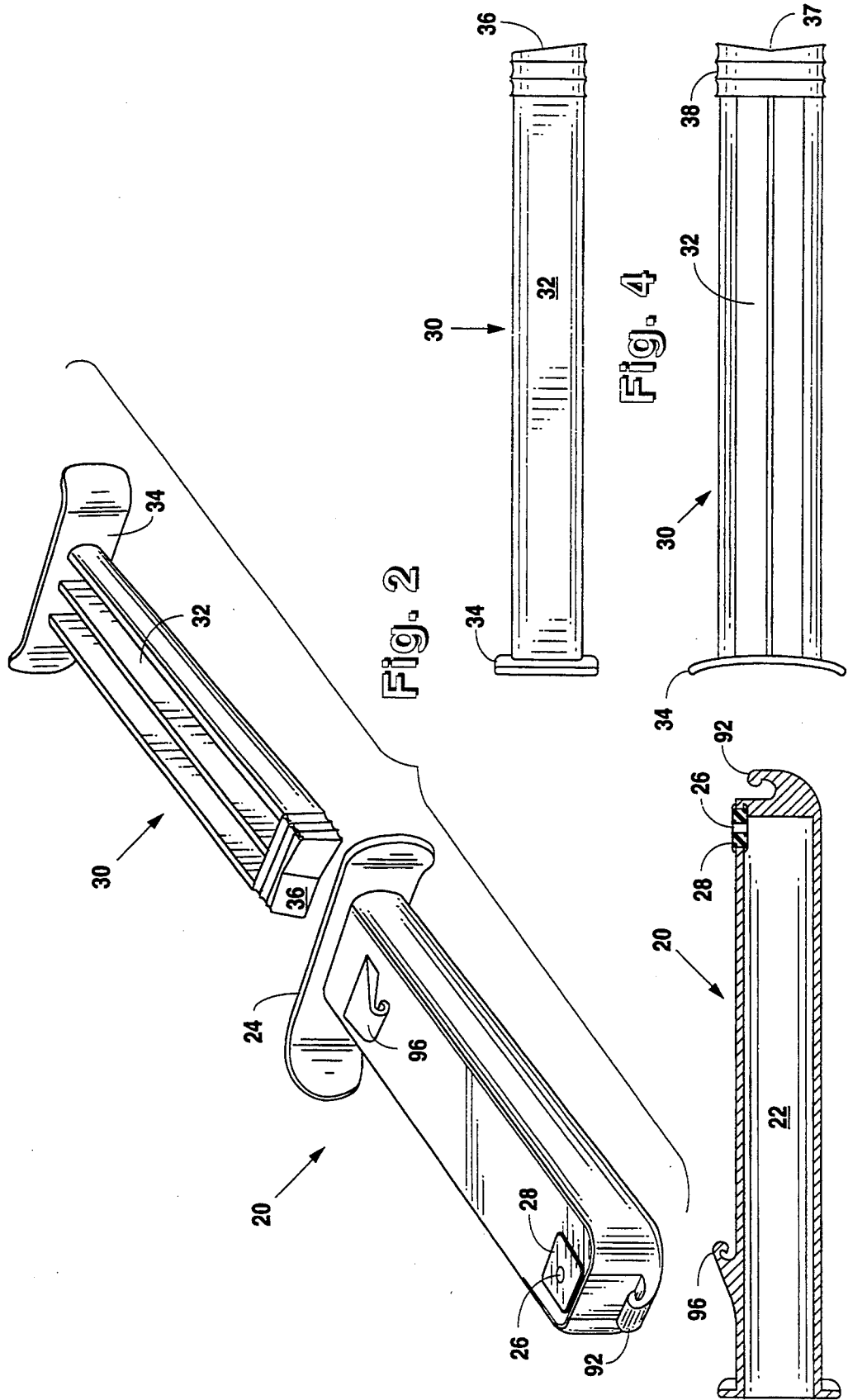

SAFETY SYRINGE WITH NON-LINEAR NEEDLE

BACKGROUND OF THE INVENTION

1. Field of the Invention

This invention relates to syringes and more particularly to a safety syringe having a needle guard for reducing the risk of accidental needle sticks.

2. Background of the Invention

Most syringes used today for medical or laboratory purposes are disposable and are intended to be discarded after a single use. In a standard disposable syringe, a piston or plunger is slidable within a cylindrical fluid chamber, the shank of the piston extending beyond the rear end of the chamber and terminating in a handle. The front end of the chamber has a projecting nozzle that is coaxial with an internally threaded socket adapted to receive a needle supporting hub. When the needle supporting hub is screwed into the socket, the nozzle is then in fluid communication with the needle.

A hypodermic needle and an attached syringe are commonly distributed in sterile condition in a plastic bubble backage to protect them against contamination in storage and shipment. In addition, the hypodermic needle is enclosed in a removable protective cap or overcap whose inlet end snaps onto the needle hub. Thus, after the hypodermic needle and syringe are removed from its package, in order to put it to use one must first remove the protective cap to expose the needle. After the hypodermic needle has been injected into a patient and then withdrawn, before discarding it is preferable to place the protective cap back on the needle hub so that those thereafter handling discarded hypodermic needles for purposes of disposal will not be pricked.

Most accidental needle sticks occur when the needles are being recapped. To recap the needle one must first align the needle with the relatively small diameter inlet of the protective cap. Should the needle be misaligned, as may well happen should the handler be hurried, careless, or distracted, the point of the needle may not enter the protective cap but may instead puncture the finger of the handler.

With the increased awareness concerning the potential for transmission of AIDS and other infectious diseases from used syringes, a number of different devices have been proposed to reduce the risk of accidental needle sticks. One approach to reduce the risk of accidental needle sticks has been to provide a protective shield which is moveable between a retracted and an extended position. A number of different products have been developed to meet the requirement that the needle be permanently covered after the syringe has been used. However, many of these products involve twist-to-lock mechanisms which will often require at least two hands to operate and do not readily indicate when the shield has been locked in the extended position. Other products lock automatically when the shield is extended, however, the locking mechanism remains exposed and may be manually manipulated to retract the shield after the shield has been locked.

Furthermore, many of the products require the user to use both hands to perform complex manipulations of the safety syringe in order to move the protective shield to the extended needle protecting position. Typically, the user must hold the syringe cylinder with one hand while the other hand is used to move the protective shield distally to the extended position. In other products, the user must place their hands unacceptably close the potentially infective needle to move the protective shield to the extended position. It would be preferred for the user to be able to cover the needle by safely using only one hand.

SUMMARY OF THE INVENTION

An object of the invention is to substantially overcome the disadvantages mentioned above.

Another object of the present invention is to provide a safety syringe which can be operated with one hand and which cannot be easily manipulated to extend the needle once the needle has been placed in the retracted and protected position.

A further object of the present invention is to provide a safety syringe wherein the needle guard assembly may be easily coupled and de-coupled with the cylinder assembly.

Still a further object of the present invention is to provide a safety syringe which can be operated without the user having to place their hands near the potentially infectious needle point in order to move the needle to the retracted and protected position.

In accordance with the above objectives the present invention is disclosed as being a hypodermic syringe, with a nonlinear needle that can not be re-used once the needle has been moved to a needle protecting retracted position, and as having either an oval or rectangular cylinder and plunger for displacing the fluid within the cylinder. A rectangular needle guard with an interior chamber is demountably attached to the cylinder. The needle guard has an elongate needle assembly, having the nonlinear needle, slidably mounted within the interior chamber of the needle guard. The needle assembly also includes means for fluidly coupling the cylinder to the needle when the needle assembly is in the extended position and means for fluidly separating the cylinder from the needle when the needle assembly is in the retracted position.

Lock means locks the needle assembly in the needle exposing extended position. Release means unlocks the needle assembly allowing a coil spring to linearly move the needle assembly to the needle protecting retracted position. The spring keeps the needle in the needle protecting retracted position and from returning to the needle exposing extended position.

BRIEF DESCRIPTION OF THE DRAWINGS

FIG. 2 is an exploded front and rights side perspective view thereof.

FIG. 3 is a left side cross-sectional view of the rectangular cylinder of the present invention.

FIG. 4 is a left side elevational view of the rectangular plunger of the present invention.

FIG. 5 is a top plan view of the rectangular plunger of the present invention.

DETAILED DESCRIPTION OF THE INVENTION

Figure 1:
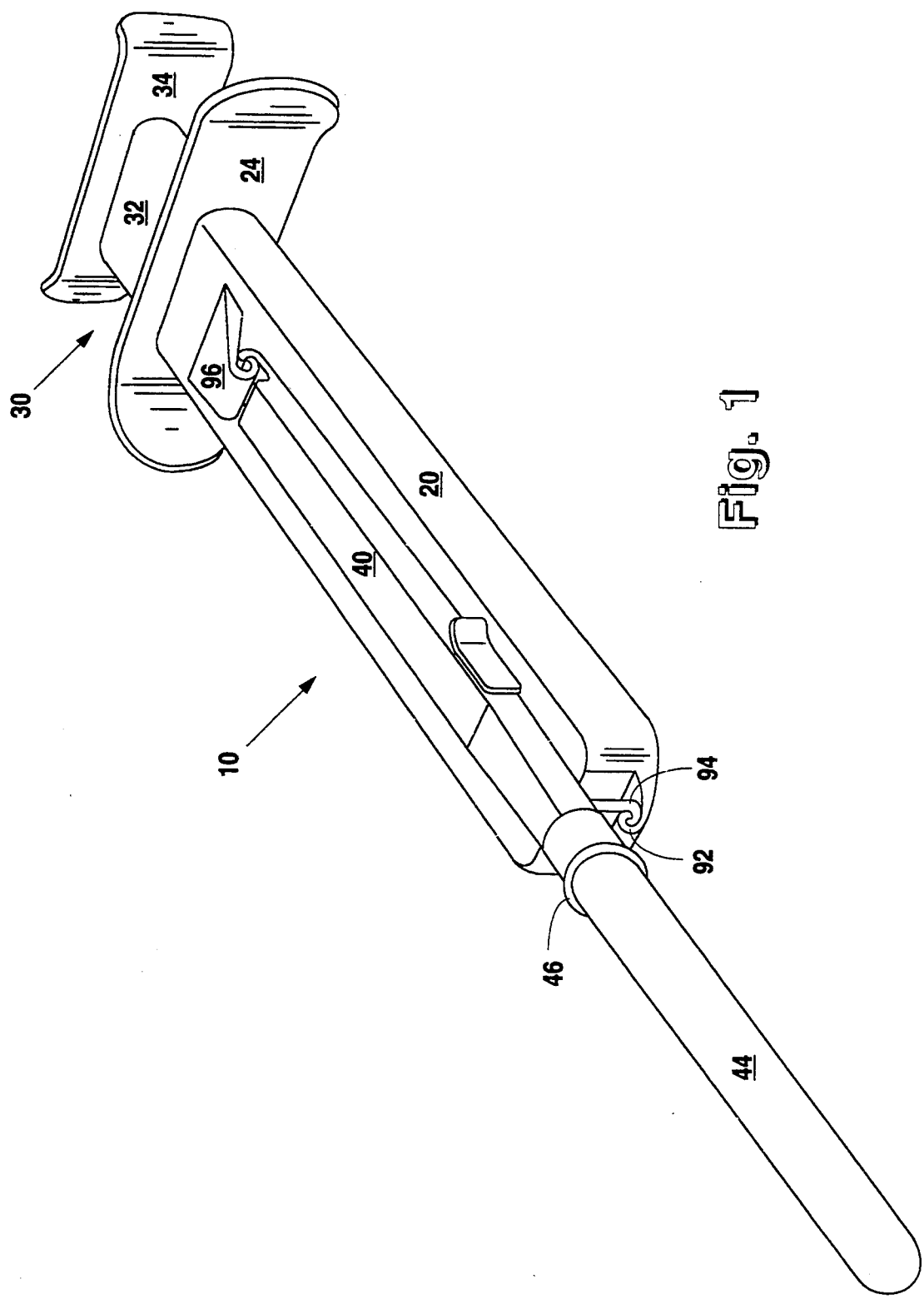
FIG. 1 is a front and right side perspective view of a rectangular safety syringe with a nonlinear needle made according to the invention.

In describing the present invention, the term "distal end" of an element refers to the end of the element farthest from the needle point of the device which is designed to pierce the skin of the patient. The term "proximal end" of an element refers to the end of the element closest to the needle point of the device which is designed to pierce the skin of the patient.

Although a rectangular shaped safety syringe (10) is illustrated in the drawings, the safety syringe could also be circular, oval or elliptical shaped. As long as the cylinder (20) and needle guard (40) are capable of being coupled with fluid communication in a side to side arrangement any shape can be incorporated. For example, the cylinder could be oval and the needle guard could be complementary arcuate shaped to allow coupling in a concave to convex manner. Or, the cylinder could be oval with one longitudinal side being flat and the needle guard could then have a complementary flat bottom side to allow coupling of the parts.

Referring to the figures, a rectangular safety syringe (10) with a nonlinear needle (62) is shown having a rectangular cylinder (20) having an interior chamber (22) for containing a fluid. The cylinder (20) is formed of transparent, synthetic plastic material such as polyethylene, polypropylene, polystyrene or PVC having indicia thereon (not shown) to indicate the level of fluid in the chamber (22). The cylinder (20) can be made to hold any amount of fluid that is desired, but typically will be made to hold either 2 cc, 5 cc, 10 cc, and 20 cc of fluid. Slidable within the cylinder (20) is a rectangular plunger (30) for ejecting fluid from the chamber (22) or drawing fluid therein, the plunger (30) having a shank (32) which extends beyond the open, distal end of the cylinder (20) and terminates in a thumb flange (34).

As is conventional, the distal end of cylinder (20) is provided with a finger flange (24) whereby if a user wants to use the syringe (10) to draw fluid from a patient or to draw fluid from a medicine vial, the user holds the finger flange (24) with the fingers of one hand while grasping the thumb flange (34) with the fingers of the other hand. If the user wants to use the syringe (10) to inject fluid into the patient, the user holds the finger flange (24) with the fingers of one hand while pushing the thumb flange (34) with the thumb of the same hand.

A fluid port (26) is located on the top side of the proximal end of the cylinder (20) to allow fluid communication to and from the interior chamber (22) of the cylinder (20). A gasket (28) may be used to ensure a seal is achieved at the fluid port (26) during fluid communications. The gasket (28) may be made of soft, pliable material such as rubber, synthetic rubber, silicon, or the like.

To facilitate fluid communication an angled plug (36) is attached to the proximal end of the plunger (30). The plug (36) is angled with conduits (37) in its face to facilitate the complete displacement of the fluid from the interior chamber (22) of the cylinder (20). The plug (36) is also ribbed (38) so that when the plunger (30) is pushed in all the way into the cylinder (20) all of the fluid in the interior chamber (22) of the cylinder (20) is forced out the fluid port (26).

Figure 6:
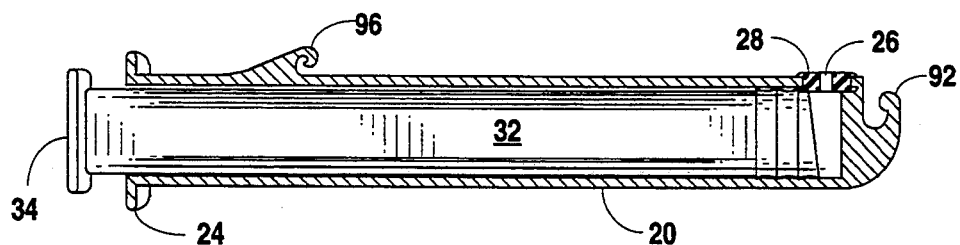
FIG. 6 is a left side cross-sectional view of the plunger inserted in the cylinder of the present invention.

The rectangular plunger (30) may have a rectangular shank (32) or, as seen in FIG. 6, it may have a central shank (32) with fins extending in four directions a sufficient distance to slidably contact the inner wall of the cylinder (20).

Figure 7:
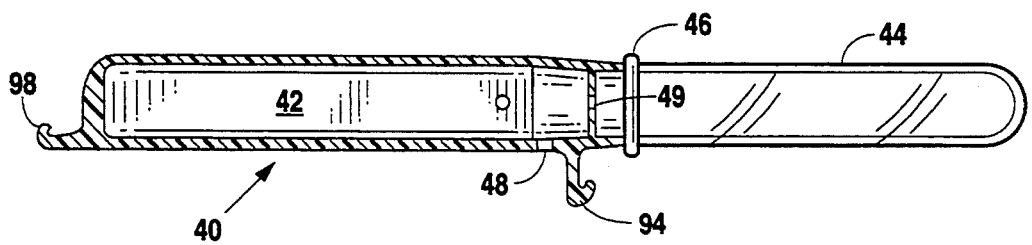
FIG. 7 is a left side cross-sectional view of the needle guard assembly without the needle assembly of the present invention.
Figure 8:
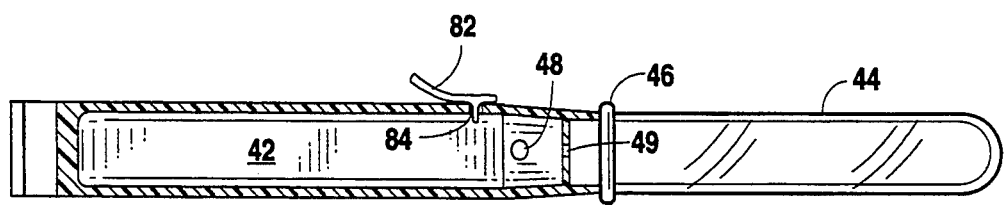
FIG. 8 is a top side cross-sectional view of the needle guard assembly without the needle assembly of the present invention.

As seen in FIGS. 1, 7 and 8, a rectangular needle guard assembly (40), having an interior chamber (42), is designed to be removably coupled to the cylinder (20). The needle guard (40) is approximately twice the length of the needle assembly (60). The needle guard (40) includes a protective cap (44) removably mounted to the proximal end of the needle guard (40) for protecting the needle (62) from contamination when the needle assembly (60) is in the extended position and prior to use. The protective cap (44) may be made of any rigid or protective material such as plastic or glass, but in the preferred embodiment it is made of plastic and is scoured (46) to easily snap off the needle guard (40) when the syringe (10) is to be used.

The needle guard (40) has a complementary fluid port (48) for fluid communication. When the needle guard (40) is coupled to the cylinder (20), the needle guard's fluid port (48) aligns with the cylinder's fluid port (26) to allow the complete displacement of the medicinal fluid in the cylinder (20) when the plunger (30) is pushed into the cylinder (20).

Figure 9:
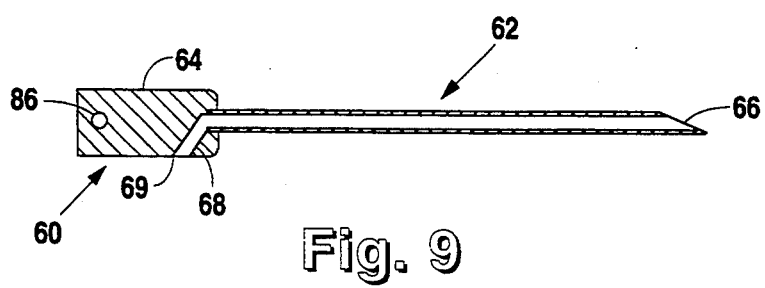
FIG. 9 is a left side cross-sectional view of the needle assembly of the present invention.
Figure 10:
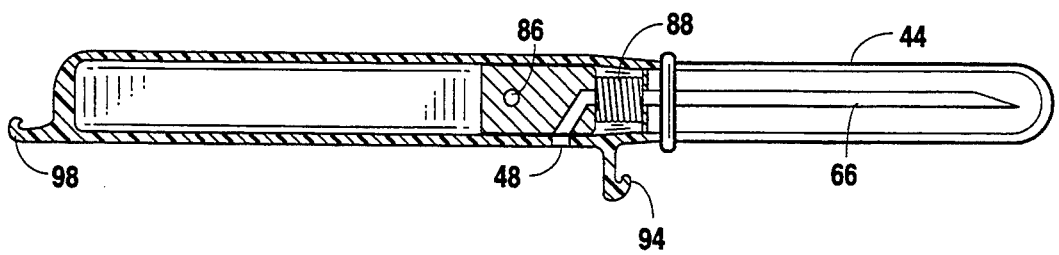
FIG. 10 is a left side cross-sectional view of the needle guard assembly, with the needle assembly in the extended and locked position, of the present invention.

As seen in FIGS. 1, 9 and 10, an elongate needle assembly (60) includes an elongate and nonlinear hollow needle (62) mounted in a needle housing (64). The needle housing (64) is slidably located within the interior chamber (42) of the needle guard (40). When delivered and prior to the syringe's use, the needle housing (64) is movable between extended and retracted positions.

The nonlinear needle (62) includes a hollow proximal needle section (66) which is preferably straight and a short hollow distal needle section (68) which is angled and which includes a funnel shaped orifice (69) to provide fluid communication between the cylinder (20) and the needle (62). The needle (62) can be made in any length and gauge as needed and still be contained in this invention.

Figure 11:
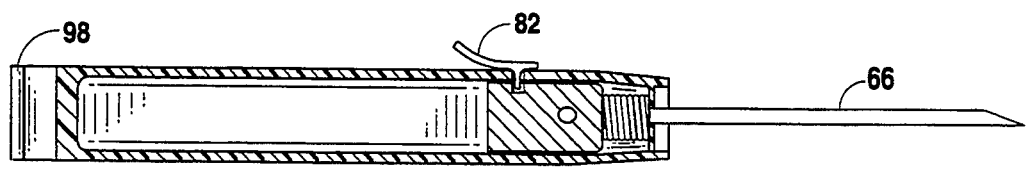
FIG. 11 is a top side cross-sectional view of the needle guard assembly, with the needle assembly in the extended and locked position and the protective cap removed, of the present invention.
Figure 12:
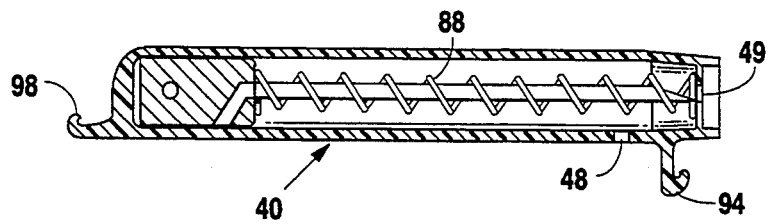
FIG. 12 is a left side cross-sectional view of the needle guard assembly, with the needle assembly in the needle protecting retracted position and the protective cap removed, of the present invention.
Figure 13:
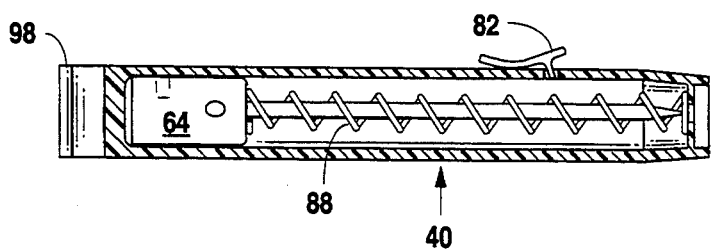
FIG. 13 is a top side cross-sectional view of the needle guard assembly, with the needle assembly in the needle protecting retracted position and the protective cap removed, of the present invention.

As best seen in FIGS. 8, 11, and 13, a lock mechanism (80) is located on the left proximal side of the needle guard (40) to lock the needle assembly (60) in the extended position. The lock mechanism (80) consists of a release tab (82) with a locking pin (84) flexibly secured to the needle guard (40) and a notch in the needle housing (64). In the locked position, the locking pin (84) is located in the notch (86) keeping the needle housing (64) from sliding. To unlock the needle housing (64), the user presses down on the release tab (82) thereby raising the locking pin (84) out of the notch (86) and allowing the needle housing (64) to slide.

To facilitate sliding of the needle housing (64), a helical compression spring (88) is slidably located within the interior chamber (42) of the needle guard (40) between the proximal end of the needle housing (64) and the proximal end of the needle guard (40). When delivered in the extended and locked position, the spring (88) is compressed between the needle housing (64) and needle guard (40). The locking mechanism keeps the spring (88) from forcing the needle housing (64) away from the proximal end of the needle guard (40). Once the release tab (82) is pressed, the locking pin (84) is removed from the notch (86) in the needle housing (64) and the spring (88) is allowed to release and forces the needle housing (64) away from the proximal end of the needle guard (40). The free length of the spring (88) is approximately as long as the length of the interior chamber (42) so that the needle housing (64) is kept at the distal end of the needle guard (40). Once the needle housing (64) is at the distal end of the needle guard (40), the needle is completely housed in the needle guard (40). A rubber seal (49) with a small opening may be located at the proximal end of the needle guard (40) to support the needle (62) and to reduce the chance of somebody getting pricked by the point of the needle (62) when the needle assembly (60) is in the retracted position.

A benefit of the present invention is that it is virtually impossible to access the needle (62) once it has been retracted into the needle guard (40). The needle guard (40) would in all probability be destroyed and made unusable if a person tried to access the needle (62).

The latching mechanism (90) to removably mount the needle guard (40) on the cylinder (20) is best seen in FIGS. 1–3 and 6–7. The cylinder (20) and needle guard (40) have at two pairs of flexible interlocking hooks. The proximal hook pair (92, 94) is the hook (92) located at the proximal end of the cylinder (20) and the hook (94) located at the proximal end of the needle guard (40). The distal hook pair (96, 98) is the hook (96) located at the distal, top end of the cylinder (20) and the hook (98) located at the distal end of the needle guard (40). In operation, the user will first interlock the distal hook pair (96, 98) by inserting the distal needle guard hook (98) at an angle into the distal cylinder hook (96). The user will then push the needle guard (40) down towards the cylinder (20) until the needle guard proximal hook (94) snaps into the cylinder proximal hook (92). To remove the needle guard (40), the steps are simply reversed.

In operation, the cylinder (20) and needle guard (40) are delivered in separate sterile packing. A user will remove the cylinder (20) and the needle guard (40) from their respective packing. Then the user will hold the cylinder (20) in one hand and using the other hand will interlock the distal hook pair (96, 98) by inserting the distal needle guard hook (98) at an angle into the distal cylinder hook (96). The user will then push the needle guard (40) down towards the cylinder (20) until the needle guard proximal hook (94) snaps into the cylinder proximal hook (92).

Once the proximal hook pair (92, 94) is snapped together, the needle guard (40) and cylinder (20) are fluidly coupled. The needle assembly (60) is in the extended position and is ready for use. The protective cap (44) is then broken off and can be thrown away if the syringe (10) is going to be used immediately. If not, the protective cap (44) can be snugly placed on or screwed on the proximal end of the needle guard (40) to protect the needle (62) until the syringe (10) is to be used.

The syringe (10) is ready for use in the normal and customary manner. The syringe (10) can be used to give a patient medicine or to get a blood sample from the patient. If medicine is to be given the user will hold the cylinder (20) with his fingers and insert the needle (62) into the patient's body. Once the needle (62) is in place the user will push the thumb flange (34) into the cylinder (20) to administer the medicine. After the medicine has been administered, the needle (62) is withdrawn from the patient's body.

To safely discard the syringe (10), the user will push down on the release tab (82) thereby releasing the spring (88) to move the needle assembly (60) to the distal end of the needle guard (40) and thereby retracting the entire length of the needle (62) into the needle guard (40). The user can retract the needle (62) once the needle clears the patient's body to reduce the risk of accidental skin pricks. If the syringe (10) does not need to be used again, the entire syringe (10) can be discarded.

Due to the innovative aspect of the present invention, a used needle can be safely covered or retracted without using two hands to perform complex manipulations of the safety syringe (10) in order to move a protective shield to the extended needle protecting position. In addition, the user does not need to place their hands unacceptably close the potentially infective needle to move the needle into a protective shield.

If the user needs to replace the needle (62), he can easily do so by applying upward force to the proximal hook pair (92, 94) thereby separating the two hooks. This will also de-couple the fluid coupling between the needle guard (40) and cylinder (20). The user will then remove the needle guard's distal hook (98) from the cylinder's distal hook (96). Now the needle guard (40) can be discarded. Another sterile needle can now be attached to the cylinder (20) if needed. If not, the cylinder (20) can also be discarded.

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the present invention. It is therefore contemplated that the following claims will cover such modifications that fall within the true scope of the invention.

I claim:

1. A safety syringe comprising:
   a cylinder having an interior chamber for containing a fluid;
   a plunger slidably mounted within the interior chamber of the cylinder for displacing the fluid within the cylinder;
   a needle guard removably coupled to a side of said cylinder, said needle guard having an interior chamber and having distal and proximal ends;
   an elongate needle assembly, including a needle housing, and an elongate and nonlinear hollow needle, slidably mounted within the interior chamber of said needle guard, said needle assembly movable between extended and irreversibly retracted positions;
   means for fluidly coupling said needle to said cylinder when said needle assembly is in the extended position and for fluidly separating said needle from said cylinder when said needle assembly is in the irreversibly retracted position;

said coupling means comprising lock means for locking said needle assembly in the extended position, said lock means being a lock pin and said needle housing having a notch adapted to receive said lock pin; a coil spring slidably located within the interior chamber of said needle guard and between said distal needle section and proximal ends of said needle guard, said coil spring biasing said needle assembly to the irreversibly retracted position; and manual release means for manually unlocking said lock means from the extended position and allowing said needle assembly to move to the irreversibly retracted position, said manual release means comprising a release tab pivotally attached to said needle guard and secured to said locking pin; whereby said needle assembly is maintained in said extended position when said locking pin is received in said notch overcoming the force of said coil spring, and said needle assembly can be moved into said irreversibly retracted position when a user presses said release tab raising said locking pin and removing said locking pin from said notch of said needle housing allowing said coil spring to move said needle assembly into said irreversibly retracted position.

2. The syringe of claim 1, wherein said needle guard includes a protective camp, said cap forming an integral part of said needle guard so as to be removable only by breaking said cap away from said needle guard, and said cap mounted to the proximal end of said needle guard for protecting said needle from contamination when said needle assembly is in the extended position.

3. The syringe of claim 1 wherein said cylinder is rectangular shaped, said plunger is rectangular shaped, and said needle guard is rectangular shaped.

* * * * *